(12) United States Patent
Sugaya

(10) Patent No.: US 10,751,340 B2
(45) Date of Patent: Aug. 25, 2020

(54) COMBINATION THERAPY TO IMPROVE BRAIN FUNCTION OR PROMOTE NEUROGENESIS FOR TREATING NEURODEGENERATIVE CONDITIONS

(71) Applicant: UNIVERSITY OF CENTRAL FLORIDA RESEARCH FOUNDATION, INC., Orlando, FL (US)

(72) Inventor: Kiminobu Sugaya, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 16/307,781

(22) PCT Filed: Jun. 6, 2017

(86) PCT No.: PCT/US2017/036220
§ 371 (c)(1),
(2) Date: Dec. 6, 2018

(87) PCT Pub. No.: WO2017/214197
PCT Pub. Date: Dec. 14, 2017

(65) Prior Publication Data
US 2019/0183898 A1 Jun. 20, 2019

Related U.S. Application Data

(60) Provisional application No. 62/346,166, filed on Jun. 6, 2016.

(51) Int. Cl.
*A61K 31/519* (2006.01)
*A61K 31/407* (2006.01)
*A61P 25/28* (2006.01)

(52) U.S. Cl.
CPC .......... *A61K 31/519* (2013.01); *A61K 31/407* (2013.01); *A61P 25/28* (2018.01)

(58) Field of Classification Search
CPC .......................... A61K 31/407; A61K 31/519
See application file for complete search history.

(56) References Cited

U.S. PATENT DOCUMENTS

| | | |
|---|---|---|
| 3,610,795 A | 10/1971 | Jacques |
| 4,959,368 A | 9/1990 | Awaya et al. |
| 9,095,573 B2 | 8/2015 | Sugaya et al. |
| 2004/0024043 A1 | 2/2004 | Greig et al. |
| 2004/0138282 A1 | 7/2004 | Greig et al. |
| 2005/0272804 A1 | 12/2005 | Bruinsma et al. |
| 2007/0071731 A1 | 3/2007 | Sugaya et al. |

FOREIGN PATENT DOCUMENTS

| | | | | |
|---|---|---|---|---|
| WO | WO-2006133876 A1 * | 12/2006 | ........... | A61K 8/4953 |
| WO | WO-2009070164 A1 * | 6/2009 | ........... | A61K 31/535 |
| WO | 20090071731 A1 | 10/2010 | | |
| WO | WO-2012170599 A1 * | 12/2012 | ............. | A61K 44/06 |

OTHER PUBLICATIONS

Bateman. The New England Journal of Medicine, 2012, 367(9), 795-804 (Year: 2012).*
PCT/US2017/036220; PCT International Search Report and Written Opinion; dated Sep. 26, 2017; 11 pages.

* cited by examiner

*Primary Examiner* — Noble E Jarrell
(74) *Attorney, Agent, or Firm* — Timothy H. Van Dyke; Beusse, Wolter, Sanks & Maire PLLC

(57) ABSTRACT

Disclosed herein are methods and materials for improving brain function and/or promoting neurogenesis m a patient suffering from impaired brain function. Specifically exemplified herein ls the co-administration of phenserine and NBI-18. A method of treating a neurodegenerative disease in a patient in need thereof, said method comprising co-administering to the patient phenserine, or pharmaceutically acceptable salt thereof, and NBI-18, or pharmaceutically acceptable salt thereof, in respective amounts and frequency such that they work together to improve brain function or induce neurogenesis in the patient.

6 Claims, 2 Drawing Sheets

COMBINATION THERAPY TO IMPROVE BRAIN FUNCTION OR PROMOTE NEUROGENESIS FOR TREATING NEURODEGENERATIVE CONDITIONS

BACKGROUND

Patients currently suffering from neurodegenerative conditions such as Alzheimer's and Parkinson's have limited treatment options. Conventional drug therapy helps delay or reduce the symptoms of disease but is unable to restore complete functionality of the brain or repair damaged tissue. Through stem cell-based therapies, scientists aim to transplant cells in order to regenerate damaged tissue and restore proper function. However, the ability of implanted cells to migrate properly to a desired locus and to differentiate into a desired cell type are fundamental and vital obstacles for implementing in cell transplantation therapy.

DEFINITIONS

Figure 1:
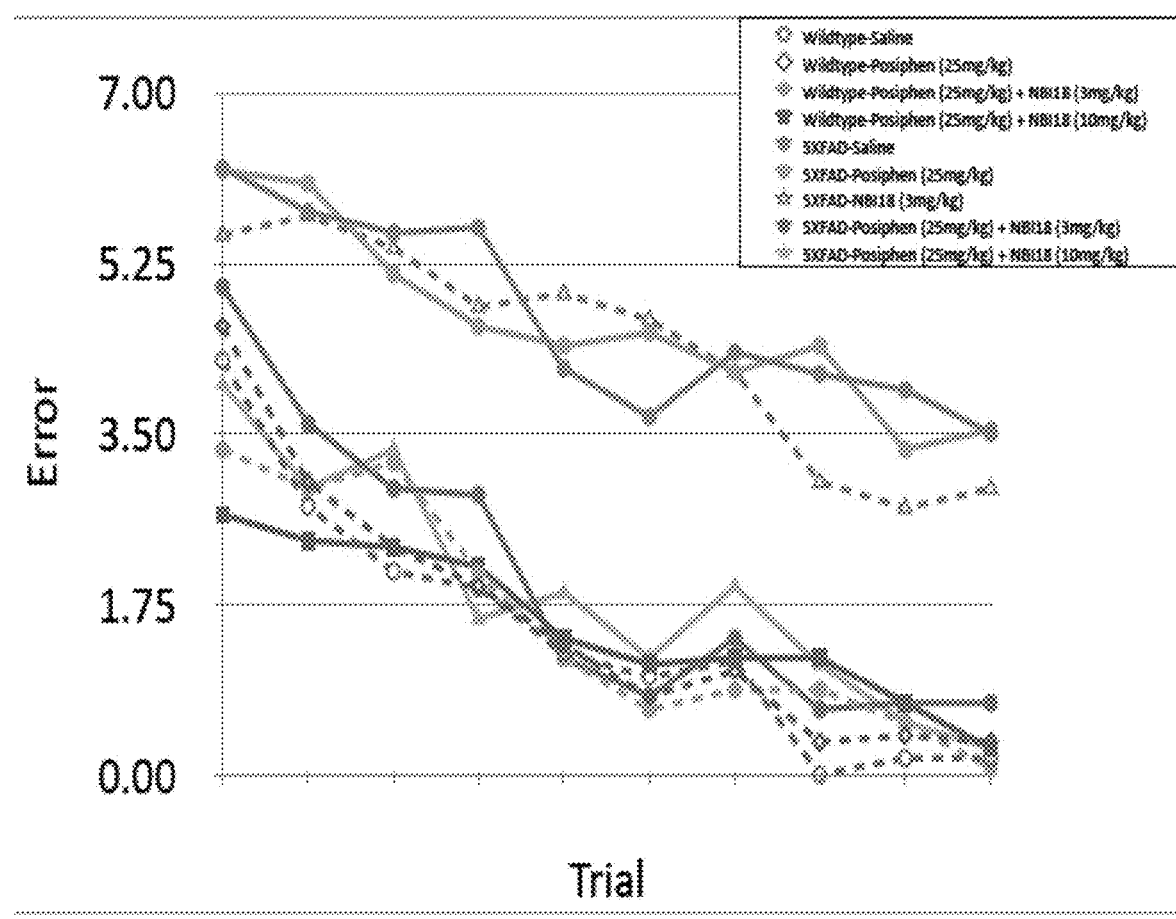
FIG. 1 Radial Water Maze testing of wild-type or 5xFAD mice treated with Posiphen or NBI-18 alone, or in combination.

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described below. However, the skilled should understand that the methods and materials used and described are examples and may not be the only ones suitable for use in the invention. Moreover, it should also be understood that as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary. Hence, where appropriate to the invention and as understood by those of skill in the art, it is proper to describe the various aspects of the invention using approximate or relative terms and terms of degree commonly employed in patent applications, such as: so dimensioned, about, approximately, substantially, essentially, consisting essentially of, comprising, and effective amount.

Generally, nomenclature used in connection with, and techniques of, cell and tissue culture, molecular biology, immunology, microbiology, genetics, protein, and nucleic acid chemistry and hybridization described herein are those well-known and commonly used in the art. The methods and techniques of the present invention generally are performed according to conventional methods well known in the art and as described in various general and more specific references, unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lan, Antibodies: A Laboratory Manual, Cold Spring Harbor Laboratory Press, Cold Spring Harbor, N.Y. (1990); Principles of Neural Science, 4th ed., Eric R. Kandel, James H. Schwartz, Thomas M. Jessell editors. McGraw-Hill/Appleton & Lange: New York, N.Y. (2000). Unless defined otherwise, all technical and scientific terms used herein have the same meaning as commonly understood by one of ordinary skill in the art.

As used herein and in the appended claims, the singular forms "a," "an," and "the" include plural references unless the content clearly dictates otherwise.

The term "about" as used herein means approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

The terms "Posiphen" and "(+)-phenserine" are used interchangeably herein and refers to a compound according to the following formula,

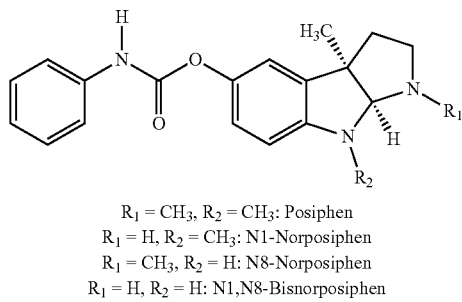

$R_1 = CH_3, R_2 = CH_3$: Posiphen
$R_1 = H, R_2 = CH_3$: N1-Norposiphen
$R_1 = CH_3, R_2 = H$: N8-Norposiphen
$R_1 = H, R_2 = H$: N1,N8-Bisnorposiphen or a pharmaceutically acceptable salt thereof. N1-Norposiphen, N8-Norposiphen and N1,N8-Bisnorposiphen are metabolites of Posiphen and unless otherwise stated are encompassed by the term Posiphen.

As used herein, the term "(−)-phenserine" mean (−)-N-phenylcarbamoyl eseroline (which may also be referred to as: (3aS)-1,3a,8-trimethyl-1,2,3,3a,8,8a-hexahydropyrrolo[2,3-b]indol-5-yl phenylcarbamate) having the following structure:

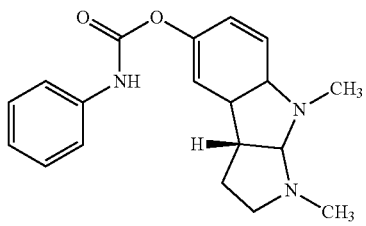 [SMILES: CN1CC[C@@H]2C3C=C(OC(=O)Nc4ccccc4)C=CC3N(C)C21]

and pharmaceutically acceptable salts and esters thereof. Also encompassed under the term (−)-phenserine are other (−) carbamates including but not limited to, (−)-2'-methylphenylcarbamoyleseroline, (−)-2'-4'-dimethylphenylcarbamoyleseroline, (−)-4'-methylphenylarbamoyleseroline, (−)-2'-ethylphenylcarbamoyleseroline, (−)-phenylcarbamoyleseroline, (−)-(−)-2',4',6'-trimethylphenylcarbamoyleseroline, (−)-2'-chlorophenylcarbamoyleseroline, (−)-2',6'-dichlorophenylcarbamoyleseroline, (−)-physovenol; (−)-5-O-

(2'-methylphenylcarbamoyl)physovenol; (−)-3,3a,8,8a-tetrahydro-3a,8-dimethyl-2H-thieno-[2,3-b]indole-5-ol butyl carbamate; (−)-3,3a,8,8a-tetrahydro-3a,8-dimethyl-2H-thieno[2,3-b]indole-5-ol heptylcarbamate; (−)-3,3a,8,8a-tetrahydro-3a,8-dimethyl-2H-thieno[2,3-b]-5-ol phenylcarbamate; (−)-3,3a,8,8a-tetrahydro-3a,8-dimethyl;-2H-thieno[2,3-b]indole-5-ol 2'-methylphenylcarbamate; (−)-3,3a,8,8a-tetrahydro-3a,8-dimethyl-2H-thieno[2,3-b]indole-5-ol 2'-isopropylphenylcarbamate; (−)-thiaphysovenine, (−)-Phenyl-thiaphysovenine; (−)-2',4'-dimethylphenyl-thiaphysovenine; heptyl-physostigmine and pharmaceutically acceptable salts or esters thereof.

The term "phenserine" as used herein refers to any of (−)-phenserine or Posiphen.

The term NBI-18 refers to heterocyclic pyrimidine molecule pertaining to the following structure

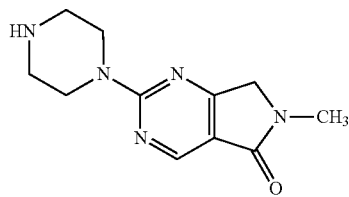 [SMILES: CN1Cc2nc(N3CCNCC3)ncc2C1=O]

or a pharmaceutically acceptable salt thereof. In a specific embodiment, NBI-18 is:

6-Methyl-2-(1-piperazinyl)-6,7-dihydro-5H-pyrrolo[3,4-d]-pyrimidin -5-one maleate

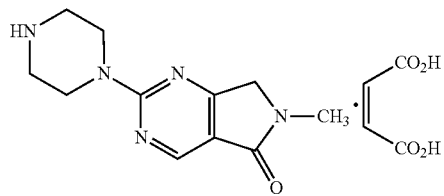

C11-H15-N5-O.C4-H4-O4; Mol wt: 349.35

Also referred in the literature as (2-piperadino-6-methyl-5-oxo-5,6-dihydro-(7H) pyrrolo-[3,4-d] pyrimidine maleate; Mwt. 349.54). Applicants cite to WO2006/133876 (PCT/EP2006/005609) for further information on pyrmidine based compounds and suitable pharmaceutical salts thereof.

The term "impaired brain function" refers to a decline in motor or cognitive function in an individual as a result of age, physical trauma or neurological condition. The term "physical trauma" denotes brain cell damage due to external sources such as blunt head trauma, severe concussion and the like. Such physical trauma can be localized or general depending on the source and severity of the trauma. Physical trauma may also involve an acute brain injury that has its origin in a biological process, for example, stroke, aneurysm, epilepsy, brain tumor, hypoxia and the like. Another source of impaired or improper brain function is neurodegenerative disease. In recent years neurodegenerative disease has become an important concern due to an expanding elderly population that is at greatest risk for these disorders. Impaired brain function can be counteracted by administration of the combination therapy of phenserine (e.g. Posiphen) and NBI-18.

The term "improving brain function" refers to increasing motor and/or cognitive function in a patient.

The term "neurodegenerative disease" refers to Alzheimer's disease, amyotrophic lateral sclerosis (ALS), Parkinson's disease, Pick's disease, Huntington's disease, progressive supranuclear palsy, corticobasal degeneration, Parkinson-ALS-dementia complex, Gerstmann-Straussler-Scheinker syndrome, Hallervorden-Spatz disease, Kufs' disease, Wilson's disease, multiple sclerosis (MS), late-onset metachromatic leukodystrophy and adrenoleukodystrophy. The effects of these diseases can be counteracted by administration of the combination therapy of Posiphen and NBI-18.

The term "co-administration" or "co-administering" as used herein refer to the administration of a substance before, concurrently, or after the administration of another substance such that the biological effects of either substance overlap.

The term "neurogenesis" refers to production of new neuronal cells in the central nervous system of a subject.

The term "therapeutically effective amount" refers to a dosage amount and/or frequency that is effective to improve brain function or induce neurogenesis, or both.

The term "active agent" refers to any of phenserine, Posiphen, (−)-phenserine, or NBI-18.

The term "pharmaceutically acceptable carrier" as used herein refers to one or more formulation materials suitable for accomplishing or enhancing the successful delivery of the active agents according to the disclosed methods.

DETAILED DESCRIPTION

In reviewing the detailed disclosure which follows, and the specification more generally, it should be borne in mind that all patents, patent applications, patent publications, technical publications, scientific publications, and other references referenced herein are hereby incorporated by reference in this application, in their entirety to the extent not inconsistent with the teachings herein.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

It has long been suggested in the literature that stem cell therapy may be useful for treatment of Alzheimer's disease (AD). However, ethical and practical issues prevent the clinical use of stem cells for AD therapy. Recently, we developed a drug, NBI-18, which significantly increases endogenous neural stem cells (NSCs). This may eliminate the need of stem cell transplantation to treat AD. Furthermore, NBI-18 can be oral administered to increase neurons, while other substances to increase NSCs has to be injected in to the brain because they do not penetrate through blood-brain-barrier to the brain. Thus, it could be used for early stage or prevention of AD. Amyloid-β (Aβ) plaque formation in the brain is one of hallmark of AD. In previous study we found that high concentration of amyloid precursor protein (APP), which produces Amyloid depositions in the brain, causes glial differentiation of neural stem cells (NSCs). See U.S. Pat. No. 9,095,573. This APP effect may be a problem for AD stem cell therapy, because we may not be able to regenerate neurons even after we increased NSCs by NBI-18 treatment. Treatment with posiphen, which was developed by a NIH chemist, Nigel Greig, shows reduction of APP in AD model animals and patients. We hypothesize that combination of NBI-18, which increases stem cells in the brain, and posiphen, which increase neural development of NSCs, will improve cognitive function in AD model mice by regeneration of neurons. We tested our hypothesis by evaluating performance on memory tasks and neurogenesis in the brain of transgenic AD model mouse. After completion of the memory testing we investigated the progression of AD pathologies and neurogenesis by immunohistochemistry of the brain of the animals. We found that the combination drug treatment of (+)-phenserine and NBI-18 increased neural stem cell production and recovers behavioral and AD pathologies in AD model mice. We found that the animals treated with the combination of a NBI-18 and (+)-phenserine had more neurogenesis in the brain and performed better in memory tasks, compared to the untreated AD model animal group. Confirmation of our hypothesis could lead to potential treatment options for human AD patients and improve their quality of life.

The administration of cholinesterase inhibitors such as (−)Phenserine is believed to be useful in treating cognitive disorders such as Alzheimers disease. The potential positive effects of administering cholinesterase inhibitors is somewhat offset by undesired and potentially dangerous side effects. The administration of cholinesterase inhibitors is believed to increase acetylcholine levels in the brain, which is depleted in an Alzheimers brain, and therefore increase activity of the brain's cholinergic system. However, such inhibitors produce a toxicity caused by their inhibition of acetylcholinesterase, such as nausea, vomiting, dizziness, tremors, bradycardia, inter alia. Some in the field have tried using an enantiomer of (−) phenserine in an effort to avoid some of these undesired side effects. For example, Greig et al., U.S. Patent Pub. 2004/0024043 AND 2004/0138282 discuss use of (+) phenserine which lacks cholinesterase activity, avoiding the side effects of the cholinesterase inhibitors. Greig et al. demonstrated that administration of (+) phenserine dramatically reduces βAPP levels in the brain. It is believed that this lowering of βAPP levels in the brain in turn results in lowered Aβ levels. Aβ is believed to induce progressive neurodegenerative condition leading to loss of memory characterized by the appearance of senile plaques that are primarily composed of an Aβ and neurofibrillary tangle aggregates. However, in certain embodiments, (−)-phenserine is co-administered with NBI-18 to treat a neurodegenerative disease. Co-administering NBI-18 with (−)-phenserine allows for administration of a lower dose of (−)-phenserine, which in turn, ameliorates the side effects commonly associated with (−)-phenserine.

Accordingly, in one embodiment, phenserine is co-administered with NBI-18 at therapeutically effective amounts to improve brain function. Improvement of brain function may be a direct result of increasing neurons in a subject's brain. In one embodiment, phenserine is Posiphen. In an alternative embodiment, phenserine is (−)-phenserine.

The phenserine and NBI-18 may be administered in separate compositions or together in the same composition. Either agent may be administered separately or together through various routes, including, but not limited to, oral, subcutaneous, intramuscular, intravenous, intra-cranial, subdermal, peritoneal, intra-ocular, transdermal, etc. In a specific embodiment, phenserine and NBI-18 are co-administered by oral administration or parenteral injection.

An embodiment of a pharmaceutical preparation includes a pharmaceutically acceptable carrier and Posiphen or its pharmaceutically acceptable salt and/or NBI-18 and its pharmaceutically acceptable salt. The pharmaceutically acceptable salt includes acid addition salts or quaternary ammonium (or amine) salts. Another embodiment pertains to a pharmaceutical preparation that includes a pharmaceutically acceptable carrier and (−)-phenserine or its pharmaceutically acceptable salt and/or NBI-18 and its pharmaceutically acceptable salt.

Pharmaceutical compositions optimally comprise a therapeutically effective amount of the active agents in admixture with a pharmaceutically or physiologically acceptable formulation agent selected for suitability with the mode of administration. Acceptable formulation materials preferably are nontoxic to the stimulated cells and the recipients at the dosages and concentrations employed.

The pharmaceutical compositions of the disclosure may contain formulation materials for modifying, maintaining, or preserving, for example, pH, osmolarity, viscosity, clarity, color, isotonicity, odor, sterility, stability, rate of dissolution or release, adsorption, or penetration of the composition, as well as proliferation, migration and differentiation capacity of the stimulated cells of the disclosure. Suitable formulation materials include, but are not limited to, amino acids (such as glycine, glutamine, asparagine, arginine, or lysine), antimicrobial compounds, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; trimethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants. See REMINGTON'S PHARMACEUTICAL SCIENCES (18th Ed., A. R. Gennaro, ed., Mack Publishing Company 1990).

The primary vehicle or carrier in a pharmaceutical composition may be either aqueous or non-aqueous in nature. For example, a suitable vehicle or carrier for injection may be water, physiological saline solution, or artificial cerebrospinal fluid. Optimal pharmaceutical compositions will be determined by a skilled artisan depending upon, for example, the intended route of administration, delivery format, desired dosage and recipient tissue. See, e.g., REMINGTON'S PHARMACEUTICAL SCIENCES, supra. Such compositions may influence the physical state, stability, and effectiveness of the composition.

Examples of the pharmaceutically acceptable salts of the active agents include hydrochlorides, hydrobromides, sulfates, bisulfites, phosphates, acidic phosphates, acetates, maleates, fumarates, succinates, lactates, tartrates, benzoates, citrates, gluconates, glucanates, methanesulfonates, p-toluenesulfonates and naphthalenesulfonates which are formed from acids capable of forming pharmaceutically acceptable anion-containing nontoxic acid addition salts, hydrates thereof, and quaternary ammonium (or amine) salts or hydrates thereof.

The composition of this invention may be formulated into tablets, capsules, powders, granules, troches, cachet wafer capsules, elixirs, emulsions, solutions, syrups, suspensions, aerosols, ointments, aseptic injectables, molded cataplasmas, tapes, soft and hard gelatin capsules, suppositories, and aseptic packed powders.

Both solid and liquid compositions may contain the aforesaid fillers, binders, lubricants, wetting agents, disintegrants, emulsifying agents, suspending agents, preservatives, sweetening agents and flavoring agents. The composition of this invention may be formulated such that after administration to a patient, the active compound is released rapidly, continuously or slowly.

In the case of oral administration, the phenserine or NBI-18, or both, are mixed with a carrier or diluent and formed into tablets, capsules, etc. In the case of parenteral administration, the active agent is dissolved in an aqueous (e.g. glucose, isotonic salt water, sterilized water or a like liquid) or non-aqueous solution of, and enclosed in vials or ampoules for injection. Advantageously, a dissolution aid, a local anesthetic agent, a preservative and a buffer may also be included into the medium. To increase stability, it is possible to lyophilize the present composition after introduction into a vial or ampoule. Another example of parenteral administration is the administration of the pharmaceutical composition through the skin as an ointment or a cataplasm. In this case, a molded cataplasm or a tape is advantageous.

The composition of this invention contains 0.1 to 2000 mg, more generally 0.5 to 1000 mg, of the active component for each unit dosage form.

The active agents may be effective over a wide dosage range. For example, the amount of either Posiphen or NBI-18 administered for one day usually falls within the range of 0.003 mg/kg to 100 mg/kg. The amount of the compound to be actually administered is determined by a physician depending, for example, upon the type of the compound administered, and the age, body weight, reaction, condition, etc. of the patient and the administration route.

In an alternative embodiment, NBI is co-administered with both Posiphen and (−)-phenserine. In this embodiment, the invention provides a dosage of (−)-phenserine of about 5 mg, about 10 mg or about 15 mg bid. The (−)-phenserine may be co-administered with about 50 mg, about 100 mg, 150 mg, about 200 mg, about 250 mg, about 300 mg, about 350 mg, about 400 mg, about 450 mg, or about 500 mg of (+)-phenserine. By combining the AChEI activity of (−)-phenserine with (+)-phenserine, β-APP and/or Aβ levels can be decreased, without inducing undesirable side effects associated with cholinergic overstimulation. For example, (+)-phenserine may be co-administered with (−)-phenserine in a ratio of about 1:1, about 2:1, about 3:1, about 4:1, about 5:1, about 6:1, about 7:1, about 8:1, about 9:1, about 10:1, about 15:1, about 20:1, about 25:1, about 30:1, about 35:1, about 40:1, about 45:1, about 50:1, about 55:1, about 60:1, about 65:1, about 70:1, about 75:1, about 80:1, about 85:1, about 90:1, about 95:1 and/or about 100:1 (wt/wt), where the weight is based on the weight of the active compound.

Conversely, the co-administration of Posiphen and (−)-phenserine (with NBI-18) occurs in non-equal molar amounts, for example about 2:1, about 3:1, about 4:1, about 5:1, about 6:1, about 7:1, about 8:1, about 9:1, about 10:1, about 15:1, about 20:1, about 21:1, about 22:1, about 23:1, about 24:1, about 25:1, about 26:1, about 27:1, about 28:1, about 29:1, about 30:1, about 31:1, about 32:1, about 33:1, about 34:1, about 35:1, about 36:1, about 37:1, about 38:1, about 39:1, about 40:1, about 45:1, about 50:1, about 55:1, about 60:1, about 65:1, about 70:1, about 75:1, about 80:1, about 85:1, about 90:1, about 95:1 and/or about 100:1, wherein the ratio is expressed as the number of moles of each active compound. In an exemplary embodiment, the invention relates to a ratio of (−)-phenserine to (+)-phenserine that is not at a ratio of about 1:1.

The compounds of the present invention can be administered in vivo to a subject in need thereof by commonly employed methods for administering compounds in such a way to bring the compound in contact with cells. The compounds of the present invention can be administered orally, parenterally, transdermally, extracorporeally, topically or the like, although oral or parenteral administration is typically desired. Parenteral administration of the compounds of the present invention, if used, is generally characterized by injection. Injectables can be prepared in conventional forms, either as liquid solutions or suspensions, solid forms suitable for solution of suspension in liquid prior to injection, or as emulsions. As used herein, "parenteral administration" includes intradermal, subcutaneous, intramuscular, intraperitoneal, intravenous, intra-articular and intratracheal routes. Additionally, the compound can be administered via a slow release or sustained release system such that a constant dosage is maintained. See, e.g., U.S. Pat. No. 3,610,795, which is incorporated by reference herein in its entirety. The compounds can also be administered using polymer based delivery systems, including, for example, microencapsulation, which techniques are well known in the art.

The effective dose of phenserine for mammals, for example, a human, may vary due to such factors as age, weight, activity level or condition of the subject being treated. Typically, an effective dosage of a compound according to the present invention is about 1 to 800 milligrams when administrated by either oral or rectal dose from 1 to 3 times daily. This dosage is typically about 0.002 to about 50 milligrams per kilogram of the subject's weight administered per day. Preferably, from about 10 to about 300 milligrams are administered orally or rectally 1 to 3 times a day for an adult human. The required dose is considerably less when administered parenterally. Preferably, from about 0.01 to about 150 milligrams may be administered intramuscularly or transdermally, one or two times a day for an adult human.

The above dosage range, therefore, does not limit the scope of the invention. The suitable number of administrations is 1 to 6, usually 1 to 4, daily.

EXAMPLES

Example 1—Behavioral and Immunochemical Tests Using Combination of Posiphen and NBI-18

Materials and Methods
Animals.
B6SJL-Tg(APPSwFlLon,PSEN1*M146L*L286V) 6799Vas/Mmjax transgenic (5xFAD) mice, which have 5 familial AD (FAD) mutant human genes, show pathological and behavioral signs of AD, including Aβ deposition at 2 months and progressive deficits in behavior. 5xFAD mice have successfully modeled behavior deficits seen in Alzheimer's disease in previous studies, and have been previously evaluated using the Morris water maze, open field test, and radial arm water maze. We purchased 2 males and 4 females heterozygous 5xFAD mice as breeders. We housed breeders in pairs of one male and 2 females. Gestation lasts 19-21 days. Pups (about 5-6 in each delivery) were weaned at (removed from breeding cage and separated) at 3 weeks of age. Tissue for genotyping was collected at the same time that ID numbers are applied. The genotyping was performed by PCR amplification of the 5xFAD gene. We used male 5xFAD mice (8 months old) for this study.

The radial water maze test was performed using a maze with six arms (32 cm length and 19 cm width) radiated from the central circular region (36 cm diameter) placed in a circular pool (100 cm diameter). A clear round platform (9 cm diameter) was placed in one of the arms at 1.5 cm beneath the surface of the water, which was opacified with nontoxic white paint. The water was kept between 22-25° C. Surrounding the pool, a visual cue was placed at each end of the radial arms. Each session consists of four acquisition trials (T1-T4), followed by a 30-min delay interval and then a retention trial (T5). For each session, an escape platform was placed at the end of the goal arm, which was different between sessions. At the beginning of each trial, the mice were placed at the end of one of the remaining five non-goal arms. The mouse was positioned facing the wall, away from the center. Each trial lasts 60 seconds, during which an animal was allowed to swim in order to find the platform. The latency to locate the submerged platform and the number of entries to the non-goal arms were recorded as errors. The error occurs when the animal's full body length enters into an incorrect arm, including the goal arm if the platform was not found. The mice were allowed to swim to the end of the incorrect arm, and then gently guided back to the starting location after every error. Once the mouse finds the platform, he was permitted to rest for 30 seconds on the platform before beginning the next trial for T1-T4. If mouse fails to find the platform within 60 seconds, the mouse was guided to the platform and allowed to rest for 30 second on the platform. The procedures for T5 was identical to T1-T4. Only one session per day was performed. The Pre-treatment sessions continue for a total of 14 days until all mice perform at an average of two or fewer errors across T4 and T5. Once mice reach the criterion for the pre-treatment behavioral testings, posiphen (25 mg/kg) was injected (s.c.) once a day for 7 consecutive days; followed by a combination of posiphen (25 mg/kg) and NBI-18 (0, 3, 10 mg/kg) was, injected (s.c.) once a day, for seven consecutive days; followed by another series of posiphen (25 mg/kg) injections (s.c.) once a day, for seven consecutive days. On the final two days of the combination injections, an injection of BrdU (100 mg/kg) was administered separately (s.c.) once per day. After the drug treatment, the animal behavior was tested again using water radial maze once a week for 6 weeks. Then the animal was euthanized and the brains were harvested for further immunocytochemistry to confirm neurogenesis in the brain by immunohistochemistry for βIII-tublin (neuronal marker), GFAP (glial marker) and BrdU (marker for newly produced NSCs).

Results

We initially use heterozygous animals to breed, resulting in 1/4 homozygous 5xFAD, 1/2 heterozygous 5xFAD and 1/4 wild type pups were produced in each delivery of about 6 pups. Since the half of them were female, which we could not use in this project, it took us 3 months to produce enough males (32 wild type and 32 5xFAD mice) to conduct preliminary study and we had to wait 8 months to start the first trial. In the preliminary maze trial we found so much variations in the behavior of the 5xFAD mice group. They were mix of homozygous and heterozygous 5xFAD mice since we cannot differentiate homozygous and heterozygous 5xFAD genes using PCR. Then we decided to use only 5xFAD heterozygous mice and restarted the breeding colony using 5xFAD heterozygous males and wild type females. To make the second batch of animal it took 4 weeks to produce 32 wild type and 32 5xFAD mice since we were able to make more breeding pairs. Then we waited another 8 moths to conduct the second study. Since then we are continuously increasing animal number of the study groups. Up to this time, we bred 492 mice (254 females, 238 males) in the current batch without counting the first batch of 211 mice. Out of the 238 males we had 29 mutant mice (albino), which we could not use for the study since they have genetic deficit in their vision. We lost 17 mice during the 8 month aging and experimental period by fighting, seizures and unknown causes. Currently we have 44 mice waiting to become 8 months old and 2 sets of breeding colones with purchasing 4 young females.

FIG. 1. Results of radial water maze. Y axis shows number of errors in the trial. 5xFAD treated with saline (control), 5xFAD treated with Posiphen (25 mg/kg) and 5xFAD treated with NBI-18 (3 mg/kg) showed significant memory deficit compare to the wild type (normal) animals while treatment with combination of Posiphen (25 mg/kg) and NBI-18 (3 mg/kg or 10 mg/kg) significantly improved the memory of 5xFAD mice and they behaved just like the normal mice.

Figure 2:
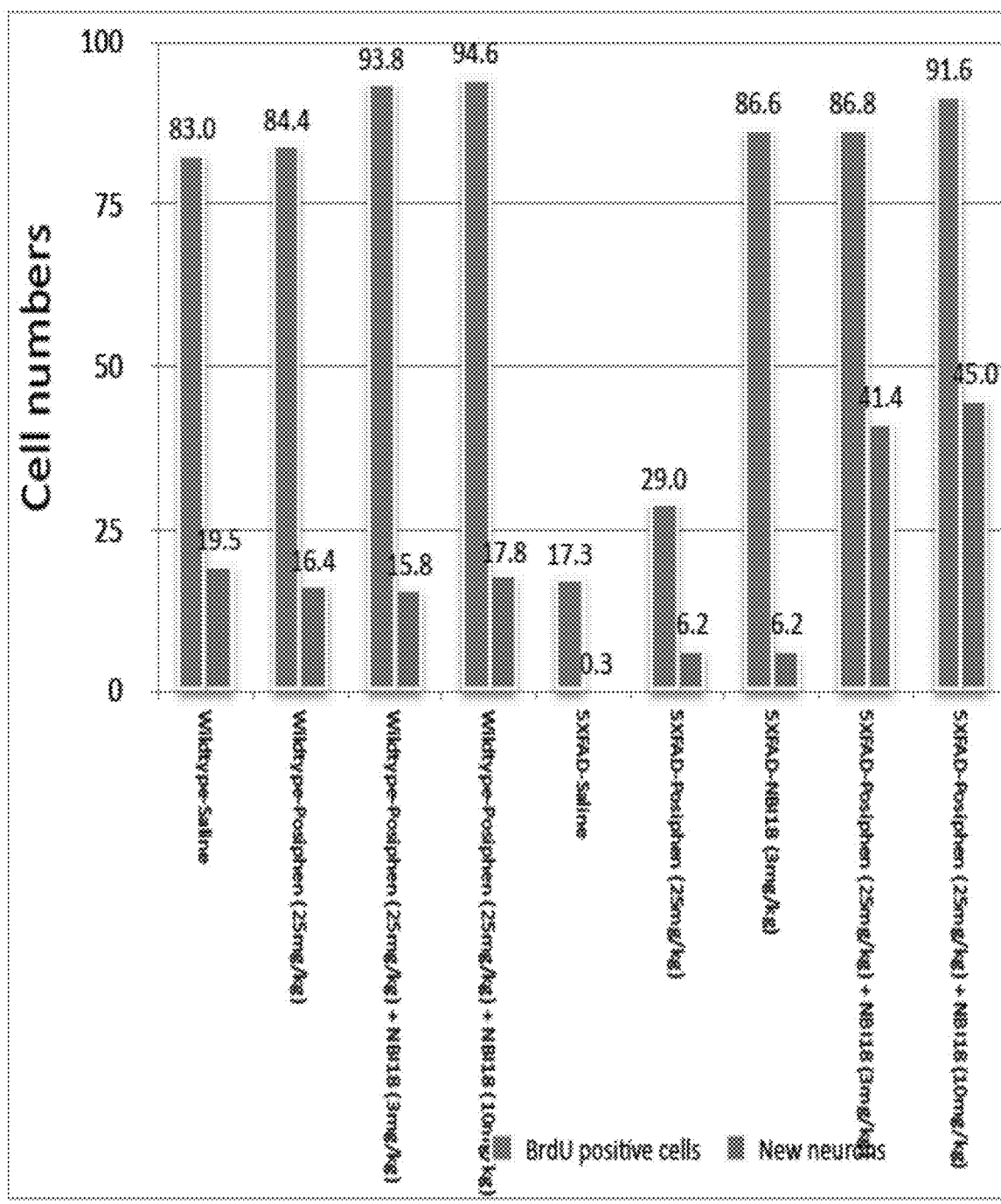
FIG. 2. Effect of NBI-18 and Posiphen treatment on neural stem cells and new neurons numbers in single cortex and parietal cortex of the animals.

The behavioral study results indicate that just increasing stem cell number by NBI-18 does not help to improve memory function in the AD model animals but the combination treatment of NBI-18 and Posiphen, which reduce, AD pathology (reducing amyloid precursor protein (APP) synthesis) significantly improve their memory and the AD animal behave just as the normal ones. Since we found that APP cause glial differentiation and prevent the neural stem cell to regenerate neurons in our previous study, the mechanism of this effect is that the reduction of APP by Posiphen allowed the newly proliferated neural stem cell to regenerate neurons, which was damaged in 5xFAD mice model. We also did not detect any significant difference between combination treatment of Posiphen (25 mg/kg) and NBI-18 (3 mg/kg) and Posiphen (25 mg/kg) and NBI-18 (10 mg/kg). This indicates that low dose of NBI-18 (3 mg/kg) is FIG. 2. Effect of NBI-18 and Posiphen treatment on neural stem cells and new neurons numbers in single cortex and parietal cortex of the animals. enough to produce maximum effect of increasing stem cell proliferation, however to confirm this we need to use lower dose of NBI-18 (0.3 mg/kg and/or 1 mg/kg) in the future study. Cell counting analysis after immunohistochemistry of the postmortem brains of the animals used in the behavioral test confirmed that NBI-18 increased stem cell proliferation and that effect is maxed out at 3 mg/kg. NBI-18 has a wide safe dose range since we have not detected any kidney or liver toxicity up to 1000 mg/kg. Without Posiphen treatment the increased number of neural stem cells does not reflect the increase of new neurons formed. This cell level analysis is highly correlate with the behavioral data, the animal showed improvement in cognition had more new neurons in their brain. Thus, the mechanism of treatments was that NBI-18 increases number of NSCs while Posiphen improve the pathological environment to increase neuronal differentiation of NSCs by reduction of APP.

Discussion

The combination treatment of Posiphen and NBI-18 may be useful to treat Alzheimer's disease. Since the mechanism of action is to regenerate neurons, which are deteriorating in the course of the disease, it has a potential of cure of AD. While other treatment currently available for clinic can only delay the progress of the diseases and may not be able to reverse the pathological changes. Since the lowest dose of NBI-18 produced maximum effect, which makes the AD transgenic model animal to be have just like normal animals, we may be able to lower the dose of NBI-18 which further increase the safety range of this compound. To confirm this combination treatment effect in human, we are start producing 3D brain in vitro models using AD patients own neural cells derived from their induced pluripotent stem cells. If we find the significant production of new neurons in this intro model after treating them with combination of Posiphen and NBI-18, we will be able to move to the clinical trial of this combination treatment in AD.

As will be apparent to one of ordinary skill in the art from a reading of this disclosure, further embodiments of the present invention can be presented in forms other than those specifically disclosed above. The particular embodiments described above are, therefore, to be considered as illustrative and not restrictive. Those skilled in the art will recognize, or be able to ascertain, using no more than routine experimentation, numerous equivalents to the specific embodiments described herein. Such equivalents are considered to be within the scope of this invention. Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways within the scope and spirit of the invention. The scope of the invention is as set forth in the appended claims and equivalents thereof, rather than being limited to the examples contained in the foregoing description.

What is claimed is:

1. A method of treating impaired brain function in a patient in need thereof, the method comprising co-administering to the patient posiphen, or pharmaceutically acceptable salt thereof, and NBI-18, or pharmaceutically acceptable salt thereof, in respective amounts and frequency such that they work together to improve cognitive function-in the patient, wherein NBI-18 comprises the following structure:

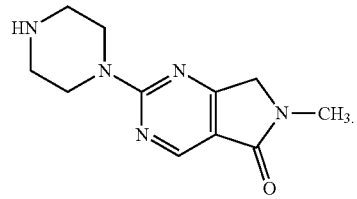 [SMILES: CN1Cc2nc(N3CCNCC3)ncc2C1=O]

2. The method of claim 1, wherein Posiphen, or pharmaceutically acceptable salt thereof, and NBI-18, or pharmaceutically acceptable salt thereof, are co-administered together by administering a composition containing both.

3. A method of treating a neurodegenerative disease in a patient in need thereof, said method comprising co-administering to the patient Posiphen, or pharmaceutically acceptable salt thereof, and NBI-18, or pharmaceutically acceptable salt thereof, in respective amounts and frequency such that they work together to improve cognitive function or induce neurogenesis in the patient, wherein NBI-18 comprises the following structure:

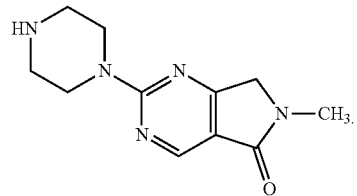 [SMILES: CN1Cc2nc(N3CCNCC3)ncc2C1=O]

4. The method of claim 3, wherein Posiphen, or pharmaceutically acceptable salt thereof, and NBI-18, or pharmaceutically acceptable salt thereof, are co-administered together by administering a composition containing both.

5. The method of claim 1, wherein the Posiphen or NBI-18 is administered orally or parenterally.

6. The method of claim 3, wherein the patient in need exhibits symptoms of Alzheimer's disease or Parkinson's disease.

* * * * *